(12) United States Patent
List

(10) Patent No.: US 10,183,113 B2
(45) Date of Patent: Jan. 22, 2019

(54) AMBULATORY INFUSION SYSTEM INCLUDING A STEP SWITCHING MECHANISM FOR VALVE CONTROL

(71) Applicant: Roche Diabetes Care, Inc., Indianapolis, IN (US)

(72) Inventor: Hans List, Hesseneck-Kailbach (DE)

(73) Assignee: ROCHE DIABETES CARE INC., Indianapolis, IN (US)

( * ) Notice: Subject to any disclaimer, the term of this patent is extended or adjusted under 35 U.S.C. 154(b) by 31 days.

(21) Appl. No.: 15/170,875

(22) Filed: Jun. 1, 2016

(65) Prior Publication Data

US 2016/0317741 A1 Nov. 3, 2016

Related U.S. Application Data

(63) Continuation of application No. PCT/EP2014/075826, filed on Nov. 27, 2014.

(30) Foreign Application Priority Data

Dec. 4, 2013 (EP) ..................................... 13195599

(51) Int. Cl.
*A61M 5/168* (2006.01)
*A61M 5/14* (2006.01)
(Continued)

(52) U.S. Cl.
CPC ...... *A61M 5/16809* (2013.01); *A61M 5/1413* (2013.01); *A61M 5/14216* (2013.01);
(Continued)

(58) Field of Classification Search
CPC .............. A61M 5/142; A61M 5/14212; A61M 5/14216; A61M 5/16809; A61M 5/1413;
(Continued)

(56) References Cited

U.S. PATENT DOCUMENTS

| 4,396,385 A | 8/1983 | Kelly et al. |
| 4,850,980 A | 7/1989 | Lentz et al. |
| 2011/0021990 A1* | 1/2011 | Navarro ............ A61M 5/14216 604/151 |

FOREIGN PATENT DOCUMENTS

| CN | 102149417 A | 8/2011 |
| CN | 102498292 A | 6/2012 |

(Continued)

OTHER PUBLICATIONS

International Search Report and Written Opinion for PCT/EP2014/075826 dated Feb. 12, 2015.
(Continued)

*Primary Examiner* — Shefali D Patel
(74) *Attorney, Agent, or Firm* — Bose McKinney & Evans LLP

(57) ABSTRACT

A dosing unit for an ambulatory infusion system, including a metering pump unit including a dosing cylinder and a piston, the piston in sealing sliding engagement inside the dosing cylinder; a valve unit having a filling port and a draining port, the filling port being couplable with a liquid drug reservoir, the draining port being couplable with an infusion site interface, and a shut-off body movable between a filling position where it couples the filling port with the dosing cylinder and a draining position where it couples the dosing cylinder with the draining port; and a valve driver coupler coupled to or integral with the shut-off body and being the output element of a step switching mechanism. Also disclosed is a drive unit that may be used in combination with a dosing unit, an ambulatory infusion system and a method for coupling a dosing unit and a drive unit.

14 Claims, 6 Drawing Sheets

(51) Int. Cl.
*A61M 5/142* (2006.01)
*A61M 5/145* (2006.01)
*A61M 39/22* (2006.01)

(52) U.S. Cl.
CPC ... *A61M 39/22* (2013.01); *A61M 2005/14573* (2013.01); *A61M 2039/226* (2013.01)

(58) Field of Classification Search
CPC ...... A61M 5/1452; A61M 2005/14533; A61M 2005/14573
See application file for complete search history.

(56) References Cited

FOREIGN PATENT DOCUMENTS

| | | |
|---|---|---|
| EP | 1970677 A1 | 9/2008 |
| EP | 2163273 A1 | 3/2010 |
| EP | 2457602 A1 | 5/2012 |
| JP | S5264022 A | 5/1977 |
| JP | H024381 A | 1/1990 |
| JP | 2012533381 A | 12/2012 |
| WO | WO 2011/010198 A2 | 1/2011 |
| WO | WO 2011010198 A2 | 1/2011 |
| WO | WO 2015/082305 A1 | 6/2015 |

OTHER PUBLICATIONS

Japanese Office Action, JP19248PCT, dated Aug. 28, 2018, (with partial human translation and machine translation), 20 pages.
Search Report of Japanese Patent Office, JP19248PCT, dated Aug. 14, 2018, (with machine translation), 21 pages.

\* cited by examiner

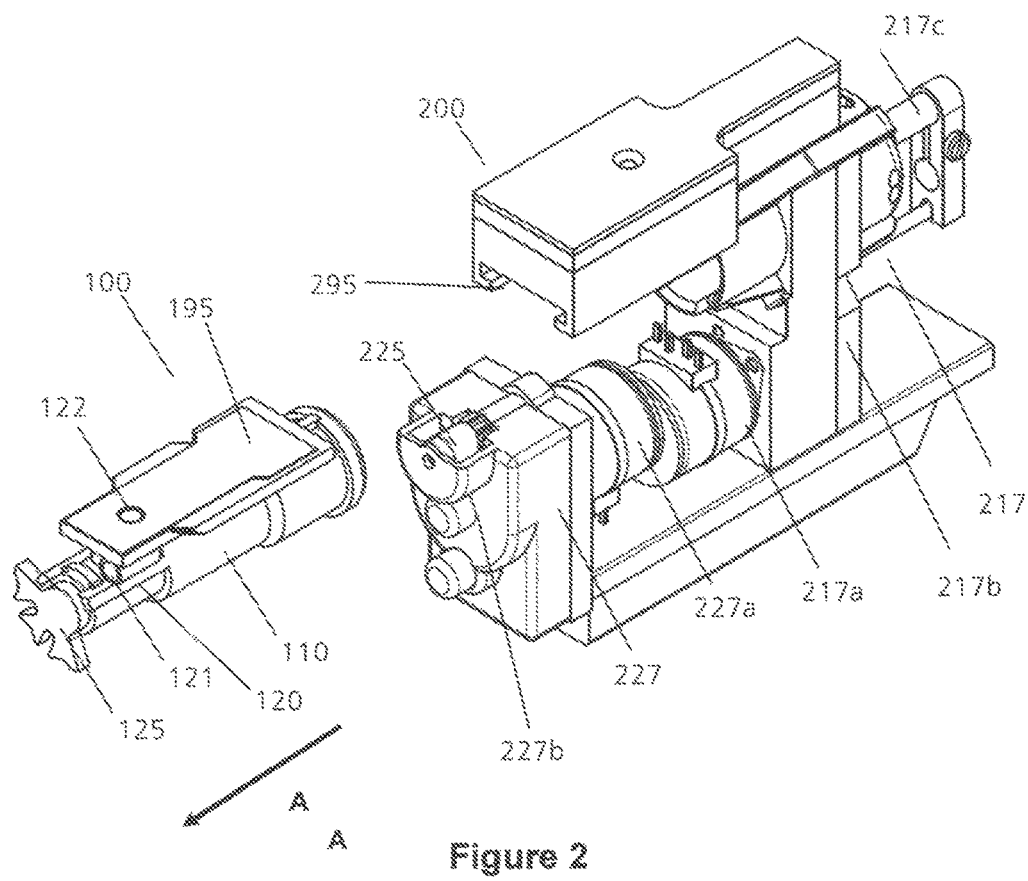
Figure 2
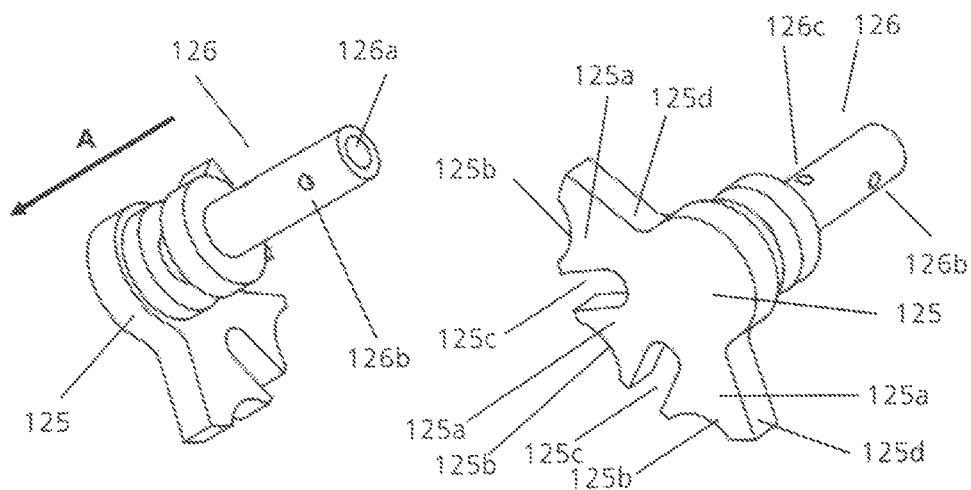
Figure 3A
Figure 3B

AMBULATORY INFUSION SYSTEM INCLUDING A STEP SWITCHING MECHANISM FOR VALVE CONTROL

RELATED APPLICATIONS

This application is a continuation of PCT/EP2014/075826, filed Nov. 27, 2014, which claims priority to EP 13 195 599.9, filed Dec. 4, 2013, both of which are hereby incorporated herein by reference in their entireties.

BACKGROUND

The present disclosure lies in the field of dosing units for an ambulatory infusion system. The disclosure lies further in the field of drive units for use in combination with a dosing unit as well as in the field of ambulatory infusion systems for infusing a liquid drug into a patient's body over an extended time period. Furthermore, the disclosure lies in the field of methods for coupling a dosing unit and a drive unit.

Ambulatory infusion devices are well known in the art for example in the therapy of diabetes mellitus by continuous subcutaneous insulin infusion (CSII) as well as in pain therapy or cancer therapy and are available from a number of supplies, such as Roche Diagnostics GmbH, Germany, or Medtronic MiniMed Inc., CA, USA.

According to a classic and well-established design, those ambulatory infusion devices or systems are typically of the syringe-driver type. A number of drawbacks of such devices are known in the art. In particular, they have a limited precision because they involve delivering very small drug amounts, typically in the nanoliter range, out of a drug cartridge having an overall drug volume in the millilitre range. Therefore, additional concepts and architectures have been proposed which use a dedicated dosing unit downstream from the drug reservoir, comprising, e.g., a micro membrane pump or a micro piston pump and are adapted to couple to a drug reservoir and especially designed for precise metering of small volumes. While several designs for such dosing units are known in the art, they are rather complex, most of them are expensive and/or critical with respect to large scale manufacture.

The EP1970677A1 discloses a system with a miniaturized metering piston pump with a dosing cylinder that is repeatedly coupled to and filled from a larger reservoir, followed by coupling the dosing cylinder to an infusion site and infusing the liquid drug out of the dosing cylinder in incremental steps and over an extended time period. For alternatively coupling the dosing cylinder to the reservoir and the infusion site, a valve system is proposed.

SUMMARY

The EP2163273A1 discloses a dosing unit according to the principles established by EP1970677A1. According to this disclosure, the dosing unit is—typically releasably—coupled to a single drive unit which is used for both piston movement and valve switching in dependence of the plunger position. Valve switching is achieved by moving, e.g., rotating, a dosing cylinder of the dosing unit relative to a stationary valve member, thus establishing alternative fluidic communication of the dosing cylinder with either an inlet or an outlet.

The present disclosure describes an alternative design for ambulatory infusion systems and its components with separate drives for piston displacement and valve switching.

In accordance with the present disclosure, a dosing unit for an ambulatory infusion system may include a metering pump unit and a valve unit. The valve unit may have a filling port, the filling port being designed for fluidic coupling with a liquid drug reservoir, and a draining port, the draining port being designed for fluidic coupling with an infusion site interface. The valve unit may further include a shut-off body, the shut-off body being movable between a filling position where it fluidic couples the filling port with a dosing cylinder of the pump unit and an alternative draining position where it fluidic couples the dosing cylinder of the pump unit with the draining port. The dosing unit may further include a valve driver coupler, the valve driver coupler being coupled to or integral with the shut-off body and being the output element of a step switching mechanism.

For operation of the dosing unit, the valve driver operatively couples to a valve actuator via a valve driver, the valve driver and the valve driver coupler, in combination, forming the step switching mechanism. As will be discussed in more detail below in the context of exemplary embodiments, coupling the valve unit with the valve actuator via a step switching mechanism provides a number of advantages. In particular, it allows the valve drive to operate with comparatively low precision requirements. Furthermore, it is favorable with respect to simple and convenient assembly and disassembly of a modular infusion system.

The pump unit may especially be designed as miniaturized piston pump with a dosing cylinder and a piston that is arranged in sealing sliding engagement inside the dosing cylinder, e.g., in a bore extending along a central axis of the dosing cylinder, i.e., coaxial with the cylinder axis. It is to be noted that the term "bore" does—here and in the following—not imply any restrictions with respect to a manufacturing process. The dosing cylinder may like other components of the dosing unit, be manufactured, for example, by machine tooling, injection moulding, 3D-printing, or other manufacturing technologies which may be used alone or in combination.

The dosing cylinder and the piston, in combination define a metering chamber of variable volume in a syringe-like way, with the volume being defined by the cross sectional area of the bore and the piston position. A fluidic coupling is present between the metering chamber and the valve unit, thus fluidic coupling the dosing cylinder and the valve unit for drawing liquid drug via the valve unit into the metering chamber and alternatively displacing liquid drug out of the metering chamber. The piston may be moved between a most distal position, corresponding to a maximum volume of the metering chamber, and a most proximal position, corresponding to a minimal and for example negligible volume of the metering chamber. The volume of the metering chamber is also referred to as the filling volume of the dosing cylinder. In a typical embodiment that may be used, e.g., in the field of CSII, the maximum filling volume may, e.g., be in a range of 10 µl to 200 µl, corresponding to 1 to 20 Units of liquid U100 insulin formulation. In particular embodiments, the maximum filling volume is in a range of 50 µl to 100 µl, e.g., 60 µl. The diameter of the bore may be in the range of some millimetres, resulting in a piston displacement in the range of millimetres to centimetres.

As will be discussed further below, the piston may be coupled to a pump drive for reciprocal displacement in incremental or virtually infinite steps, thus allowing a variation of the filling volume in incremental or virtually infinite steps.

The shut-off body may have a number of designs independent of the specific valve design. In typical embodiments, it is an axially symmetric body with a number of radial and/or axial liquid channels for controlling the flow. Favorably, at least one position of the shut-off body exists, in particular an intermediate position between the filling position and the draining position, where the pump port is neither coupled to the filling port nor the draining port and the metering chamber is accordingly fluidic isolated.

In some embodiments, the valve driver coupler includes a star wheel or star wheel section, a Geneva-type wheel or a Geneva-type wheel section. As will be discussed below in the context of exemplary embodiments, a Geneva-type wheel may be used as output element of a switching-mechanism design that is particularly suited for the present applications. Other types of step switching mechanisms, however, may be used as well.

In some embodiments, the shut-off body is designed as generally cylindrical body. The cylindrical body may exemplarily have a diameter of 3 mm or less, for example 1.5 mm. In variants, the diameter may change in a number of steps along its length or continuously, the latter resulting in a cone-shaped shut-off body. A small size of the valve and in particular of the shut-off body is favorable for a number of reasons, such as minimizing the fluidic dead volume as well as the overall dimensions.

In some embodiments, the shut-off body is made from hard material, in particular hard plastics, and a shut-off-body contacting surface of a valve housing is made from soft material, in particular rubber or thermoplastic elastomers. Other soft plastics may be used as well. Such a design is favorable with respect to sealing.

In some embodiments, the shut-off body is designed to move rotary around a valve rotation axis. For this type of embodiment, the valve unit is designed as rotary valve with the valve state being determined by the rotational position of the shut-off body relative to the valve housing. For this type of embodiment, the filling position and the draining position are rotational positions of the shut-off body where a fluidic channel of the shut-off body as described before is aligned with the filling port or draining port respectively, which are a realized as bores in the valve housing. Alternatively, however, the valve unit may be realized in different ways, e.g., as sliding valve with linear sliding shut-off body or in combination of rotational and sliding motion.

In some embodiments, the valve rotation axis is parallel or perpendicular to a piston displacement axis of the pump unit. Either of those designs which are discussed further below in more detail in the context of exemplary embodiments allows the design of a particularly compact and user-friendly design.

In some embodiments, the valve driver coupler includes a meshing slot for meshing with a meshing pin of a valve driver as driving element of a step switching mechanism.

In some embodiments, the dosing unit is designed for releasable coupling with a drive unit. Releasable coupling of the dosing unit and the drive unit allows the design of a modular ambulatory infusion system with, e.g., a durable unit that includes the drive unit and may include a user interface, control circuitry, and the like, and a disposable unit that is designed for a single application of, e.g., a number of days only and may include the dosing unit and the liquid drug reservoir. For such a modular design that is assumed in the following, controlling the valve via a step switching mechanism is particularly favorable with respect to coupling and decoupling, as will be discussed further below in more detail. Alternatively, however, the dosing unit may, fully or partly, be formed integrally with the drive unit.

The phrase "releasable coupling" accordingly refers to a design that allows mechanical coupling and decoupling of the dosing unit and the drive unit, substantially in form of a substantially rigid mechanically coupling and further enables subsequent decoupling, with the decoupling not causing damage to at least the driving unit. For this purpose, corresponding mechanical mounting structures may be provided at both the dosing unit and the drive unit as will be exemplary described further below. The mechanical coupling of the dosing unit to a drive unit favorably simultaneously couples the vale unit, in particular the valve driver coupler, with a valve drive of the dosing unit and the position with a piston drive of the dosing unit.

According to a further aspect, the present disclosure is directed towards a drive unit. The drive unit may include a pump drive, the pump drive including a pump actuator and a pump driver coupled to the pump actuator, the pump driver being designed for coupling to a piston of a metering pump unit for transmitting a pump driving force and/or pump driving torque from the pump actuator to a piston of the pump unit. The drive unit may further include a valve drive, the valve drive including a valve actuator and a valve driver coupled to the valve actuator, the valve driver being designed for coupling to a valve driver coupler of a valve unit for transmitting a valve switching force and/or valve switching torque from the valve actuator to the valve unit, wherein the valve driver is the driving element of a step switching mechanism.

In some embodiments, the valve driver includes a meshing pin for meshing with the valve driver coupler. The meshing pin is eccentric on a valve driver body. The valve driver may further include a central pin in alignment with the valve gear output shaft. In operation, the meshing pin accordingly moves on a circular path around the central pin.

In some embodiments, the drive unit is designed for releasably coupling with the dosing unit. "Releasable" is to be understood in the same sense as described before in the context of the dosing unit.

According to a still further aspect, the present disclosure is directed towards an ambulatory infusion system for infusing a liquid drug in to a patient's body over an extended time period. The infusion system may include a dosing unit and a drive unit as generally discussed before and further below in the context of exemplary embodiments.

In some embodiments, of an ambulatory infusion system, the valve driver and the valve driver coupler are in a non-meshing state upon coupling the dosing unit and the drive unit. For this type of embodiment, meshing of the valve driver and the valve driver coupler only occurs in a state where mechanical coupling between drive unit and dosing unit is already established, subsequent to a coupling movement. Thereby, the precision and alignment requirements for establishing the coupling are largely reduced.

According to a still further aspect, the present disclosure is directed towards a method for coupling a dosing unit and a drive unit as generally discussed before and further below in the context of exemplary embodiments. The method may include providing the drive unit and the dosing unit as structurally distinct units. The method may further include carrying out a coupling movement, the coupling movement bringing the drive unit and the metering pump unit into an operational relative position, the coupling movement further bringing the valve driver and the valve driver coupler into an operational relative position, wherein the valve driver and the valve driver coupler are in a non-meshing configuration during the coupling movement

BRIEF DESCRIPTION OF THE DRAWINGS

It is to be noted that in the following description, terms indicating a direction, position, or orientation, such as "left," "right," "upper," "lower," "top," "bottom" are merely intended to improve the reader's understanding and exclusively refer to the figures. They do not imply any particular directions or orientations for the application.

The above-mentioned aspects of exemplary embodiments will become more apparent and will be better understood by reference to the following description of the embodiments taken in conjunction with the accompanying drawings, wherein:

FIG. 2 shows an exemplary embodiment of a dosing unit in combination with an exemplary embodiment of a drive unit;

FIGS. 3A, 3B show an exemplary-shut-off body with attached valve driver coupler in perspective view;

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
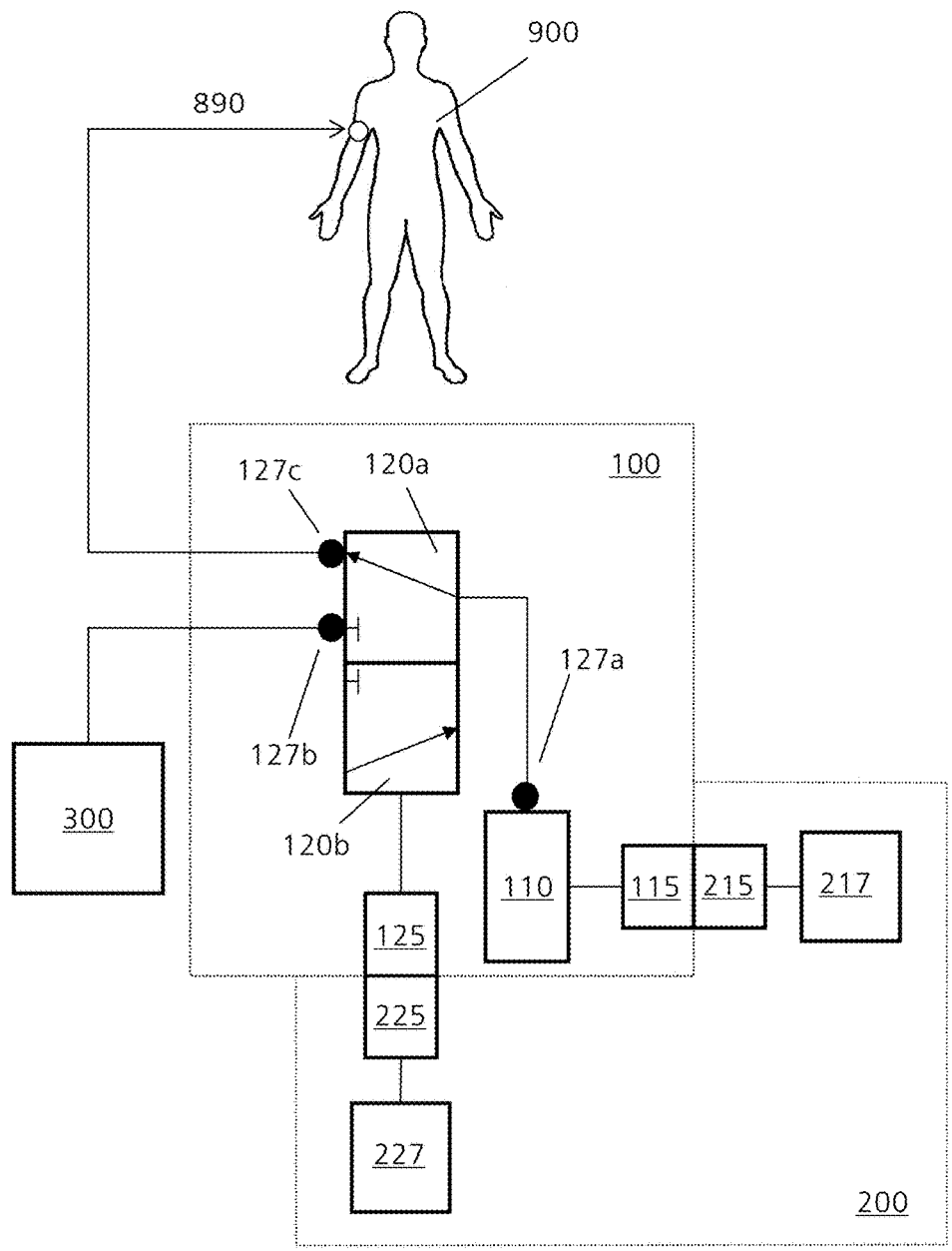
FIG. 1 shows major components of an ambulatory infusion system in accordance with the present disclosure in a simplified functional view.

FIG. 1 shows a dosing unit 100 and a drive unit 200, and a liquid drug reservoir 300. It is to be noted that only those structural and functional units are shown that are of particular relevance in view of the present disclosure. Other units, such as an electronic control unit, power supply, user interface etc. are typically present as well.

The dosing unit 100 includes a metering pump unit 110, including a dosing cylinder with a bore and a piston (elements not separately referenced) as described above in the general description. In a proximal front wall of the dosing cylinder, a bore is arranged as fluidic port that couples to the pump port 127a. The dosing unit further includes a valve unit that may alternatively be in a filling state, 120b or in a draining state 120a. During operation, the valve unit is repeatedly switched between those states. The reservoir 300 is fluidic coupled to the valve unit via a filling port 127b of valve unit. The patient 900 is fluidic coupled to the valve unit via a filling port 127c an infusion site interface 890. It is noted that the infusion site interface 890 is exemplarily shown as integral with an infusion line, e.g., a catheter. The dosing unit 100 further includes a valve driver coupler 125 for switching the valve unit between the filling position, 120b, and the draining position 120a. Similarly, the dosing unit 100 includes a pump driver coupler 115 for moving the piston of the pump unit 110 linearly inside the dosing cylinder.

With respect to the valve unit, it is further noted that FIG. 1 only shows the states 120a, 120b where either of the filling port 127b or the draining port 127c is coupled to the pump port 127a. In a further intermediate state, however, all three ports 127a, 127b, 127c are closed, resulting in fluidic isolation.

The drive unit 200 includes a pump drive 217 that is coupled to a pump drive coupler 215 as well as a valve drive 227 that is coupled to a valve drive coupler 215.

In the following, reference is additionally made to FIG. 2, showing an exemplary dosing unit 100 and a corresponding exemplary drive unit 200, with the dosing unit 100 and the drive unit 200 being part of an ambulatory infusion system according to FIG. 1. The drive unit 200 is typically designed as long-life or durable module. Like further components of an ambulatory infusion system, such as user interface and control circuitry may be designed for a life time of several months up to several years. The dosing unit 100 is typically designed as single-use module that is used continuously for a time of typically some days up to, e.g., two weeks, and is discarded afterwards. Resulting from their different application time, the dosing unit 100 and the drive unit 200 are designed for releasable mechanical and operational coupling as described before. For the mechanical coupling or mounting, the dosing unit 100 and the drive unit 200 are provided with a dosing unit mounting structure 195 and a drive unit mounting structure 295, respectively. Exemplarily, the dosing unit mounting structure 195 is realized as elongated convex structure of T-shaped cross section and the drive unit mounting structure 295 is realized as corresponding elongated concave structure of T-shaped cross section. The structures are designed with small clearance (optionally biased) sliding engagement. Additional locking elements (not shown) may optionally be provided. For coupling the dosing unit 100 and the drive unit 200, the dosing unit 100 is linearly moved in a direction against arrow A relative to the drive unit 200 such that the mounting structures 195, 295 engage. Decoupling is carried out by a corresponding linear counter-movement. In further embodiments, mechanical coupling may be sustained via a snap clamp as will be described below in the context of another embodiment, via magnetic coupling, or the like.

The direction indicated by arrow A is in the following referred to as "proximal", the direction against arrow A as "distal."

The pump unit 110 and the valve unit 120 of the dosing unit 100 are exemplarily realized as in-line design with a piston displacement axis being coincident with a valve rotation axis, parallel to arrow A, resulting in an elongated overall shape of the dosing unit 100. The valve unit 120 is arranged proximal form the pump unit 110. Both the internal structure as well as the operation of the dosing unit 100 are discussed further below with additional reference to further figures.

At the proximal end of the valve unit 120, the valve driver coupler 125 is arranged rotatable about the valve rotation axis. The valve driver coupler 125 is exemplary realized as Geneva-type wheel section with three sectors.

The drive unit 200 includes a pump drive 217 and a valve drive 227. The pump drive 217 includes a pump actuator 217a and a pump gear 217b, while the valve drive 227 includes a valve actuator 227a and a valve gear 227b. Both the pump drive 217 and the valve drive 227 are designed for reciprocal operation.

Both the pump actuator 217a and the valve actuator 227a are exemplarily realized as conventional stepper motors. Either or both of them, may, however also be realized differently, e.g., as standard DC motor, brushless DC motor, or especially designed electromagnetic drives. Optional sensors may be present for control and/or feedback purposes, but are not essential. For example, optional sensors may be provided for detecting the proximal and distal end position of the piston inside the bore of the dosing cylinder, corresponding to the minimal and maximal filling volume of the dosing cylinder, and/or a linear position sensor for substantially continuously detecting the piston. Similarly, sensors such as contacting or non-contacting end switches may be present to detect if the shut-off body of the valve unit 110 is in the filling position or the draining position, respectively.

The pump gear 217b is designed as reduction gear in form of a conventional spur gear in combination with a spindle drive and a plunger 217c, thus transforming a rotary movement of the output shaft of the pump actuator 217 into a corresponding linear displacement movement of plunger 217 in a direction parallel to arrow A. In the coupled state of dosing unit and drive unit, the axis of plunger 217c is coaxial with the bore of the dosing cylinder and the piston displacement axis. Attached to or part of the plunger 217c is the pump driver 215 (not visible in FIG. 2) that is designed for releasable coupling with a pump driver coupler that is rigidly connected to or integral with the piston (not visible in FIG. 2) of the pump unit 110. The pump driver 215 and the pump driver coupler are designed for push-pull-coupling, e.g., as bayonet coupling, snap-fit coupling, or the like. A reciprocal movement of the plunger 217c accordingly results in a corresponding reciprocal piston movement in proximal or distal direction, respectively.

The valve gear 277b is a reduction gear that is realized as conventional gear, with the valve driver 225 being coupled to or integral with an output shaft of the valve gear 227b. For the below-described design of the step switching mechanism and the valve unit, the valve gear may, e.g., be designed as four stage spur gear. It is to be noted, however, that both for the pump gear 217b and the valve gear 227b alternative designs may also be used, e.g., planetary, gears, worm gears, chain gears or other types of traction drives may be used.

Reference is additionally made in the following to FIG. 3 and FIG. 4, respectively. FIG. 3a, 3b show two perspective views of the shut-off body 126 of the valve unit 120 together with the valve driver coupler 125, with the shut-off body 126 and the valve driver coupler 125 being rigidly connected or formed in an integral way. The shut-off body 126 has a general cylindrical shape and is designed for sealing and rotational sliding reception in a corresponding bore of a valve housing. The shut-off body 126 has a central fluidic channel 126a, realized as a stud hole, and extending along a longitudinal axis of the shut-off body 126. The outlet of the central fluidic channel 126a serves as pump port 127a. The shut-off body 126 further includes two radial channels 126b, 126c perpendicular to and in fluidic communication with the central channel 126a. The radial channels 126b, 126c fluidically connect to the filling port 127b and draining port 127c, as will be explained in more detail below. Exemplarily, the radial channels 126b, 126c are arranged in a relative angle of 90°. Other angles may be used as well.

The valve driver coupler 125 is designed as Geneva-type wheel section. In the specific embodiment, a corresponding full Geneva-type wheel would have eight segments equally distributed around its circumference, while three segments 125a are actually realized for the valve driver coupler 125. The single segments 125a include concave circular peripheral faces 125b and radial faces 125d. The circular peripheral faces 125b and the radial faces 125d are connected via small intermediate peripheral faces (not referenced). Between adjacent segments 125a, the radial faces 125d form radial meshing slots 125c.

FIG. 4 shows the design of the valve driver 225 and illustrates the interaction between the step switching mechanism that is realized, in combination by the valve driver 225 and the valve driver coupler 125. The valve driver 225 includes a body 225a, a central pin 225b and an eccentric meshing pin 225c, with the single components of the valve driver 225 being rigidly connected or formed in an integral way. The valve driver 225 is rigidly coupled to the output shaft of the valve gear 227b with the central pin 225b and the output shaft being coaxial, resulting in the valve driver body 225a and the meshing pin 225c rotating about the central pin 225b upon rotation of the output shaft. As visible from FIG. 4, the central pin 225b is in fact a pin section with a segment pointing toward the meshing pin 225c being cut away. The diameter of the central pin 225b corresponds to the diameter of peripheral circular face 125, while the diameter of meshing pin 225c corresponds to the width of the meshing slots 125c, thus allowing a substantially play-free sliding engagement between meshing pin 225c and meshing slots 125c, as well as between central pin 225a and peripheral circular faces 125b.

Figure 4C:
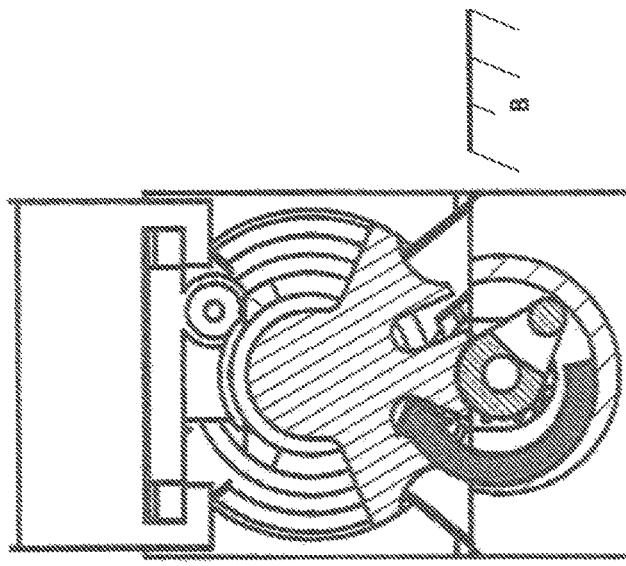
FIGS. 4A, 4B, 4C illustrate the operation of a Geneva-type mechanism as exemplary embodiment of a step switching mechanism.
Figure 4B:
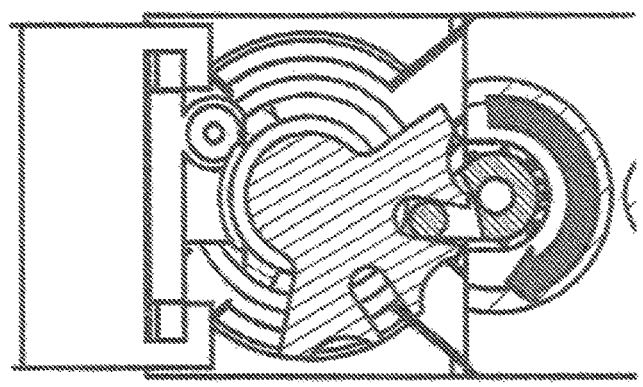
Figure 4A:
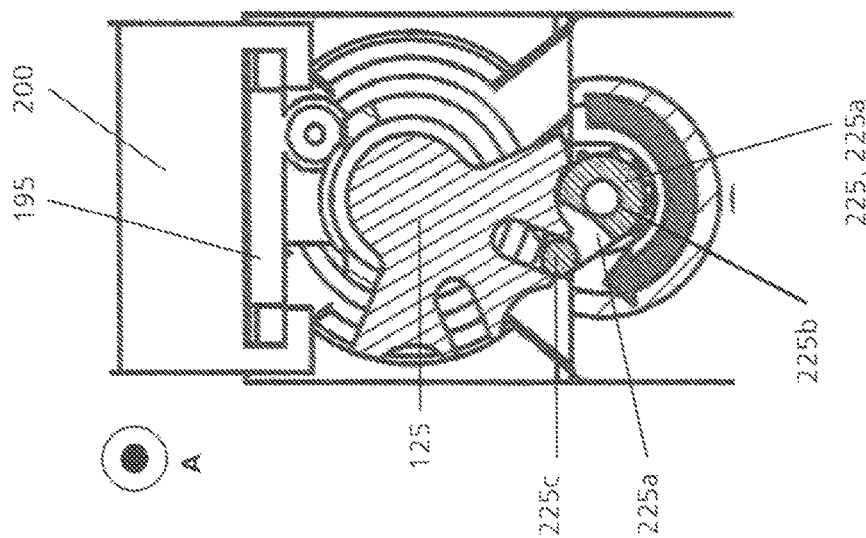

FIG. 4a shows a configuration where the valve unit 120 is in the filling position. In this state, the central pin 225b is in sliding rotational engagement with a peripheral circular face 225b. As long as the meshing pin 225c does not mesh with a meshing slot 125c, any rotation of the valve driver 225 and the holding shaft 225b does not result in any movement of the valve driver coupler 125. Via the engagement, the valve driver 125 is maintained and locked in its position.

For explaining the operation of the step switching mechanism, a clockwise rotation of the valve driver 225 is assumed, as indicated by the corresponding arrows in FIGS. 4a, 4b, 4c. FIG. 4a shows the moment where the meshing pin 225c comes into meshing engagement with a meshing slot 125c. Further rotation of the valve driver 225 results in the meshing pin 225c travelling radial inward in the meshing slot 125c and, via the sliding engagement with the slot walls, rotating the valve driver coupler 125 with the shut-off body 126 in a counter-clockwise direction.

FIG. 4b shows the configuration where the meshing pin 225c is in its most inward radial position in meshing slot 125c. Further clockwise rotation of the valve driver 225 will result in an radial outward motion of meshing pin 225c in meshing slot 125c and further counter-clockwise rotation of the valve driver coupler 125, until, finally, the meshing pin 225c leaves the meshing slot 125c, thereby ending the meshing engagement between the meshing pin 225c and the meshing slot 125c. FIG. 4c shows the configuration somewhat later where the meshing pin 225c and the meshing slot 125c are out of meshing engagement.

From FIGS. 4a, 4b, 4c it can be seen that the Geneva-type wheel of the valve driver 125 is, at all points in time, in engagement with at least one of the central pin 225b or the meshing pin 225c. Where the meshing pin 225b is in meshing engagement with a meshing slot 125c, rotation of the valve driver coupler 125 is controlled by interaction with the meshing pin 225c via positive guide. Where the meshing pin 225c does not interact with a meshing slot 125c, the valve driver coupler 125 is locked in position via engagement of the central pin 225b with a peripheral circular face 125b.

The configuration shown in FIG. 4c is an intermediate configuration where the valve unit is neither in the filling nor the draining position, but half way in between where no fluidic coupling exists between the pump port 127a and any of the filling port 127a or draining port 127c, respectively. Further clockwise rotation of the plunger driver 225 will result in the before-described sequence being repeated with the sole difference that the meshing pin 225c meshes with the other one of the two slots 125c. When the meshing pin 225c comes out of meshing engagement with this second meshing slot 125c, the valve unit 110 is in the draining position. Each full rotation of the valve driver 225 accordingly results in a rotation of the valve driver coupler 125 corresponding to an angle between adjacent Geneva-type segments 125a or meshing slots 125c, respectively.

For the exemplary design of the shut-off body as shown in FIG. 3, a sequence of successive meshing engagement and disengagement between the meshing pin 225c and both meshing slots 125c results in a total rotation of the valve driver coupler 125 and the shut-off body 126 by 90°, corresponding to the angle between the radial channels 126b, 126c, respectively. In variants, the valve driver coupler 125 may have more or less segments 125a, and switching between the filling position and the draining position may be achieved via more than one intermediate step or without any intermediate steps, as long as the total angle corresponds to the required switching angle in accordance with the shut-off body design. For a typical design of a miniaturized ambulatory infusion system, the shown exemplary design is considered as good compromise taking into account factors such as the friction forces (and thereby, energy consumption and valve actuator design), reduction rate of the valve gear and overall dimensions.

Switching the state of the valve unit back to the filling position is achieved in an analogue way by counter-clockwise rotation of the valve driver 225.

Favorably, two pairs of stops (not separately shown) are provided that limit the rotational movement between of the valve driver coupler 125 and the shut-off body 126 with respect to the valve housing such further movement of the valve driver coupler 125 and the shut-off body 126 is blocked when the shut-off body assumes the filling position or draining position, respectively. Rotational movement is accordingly restricted to the angle range between the filling position and the draining position, respectively.

For such a design including stops, simple and effective control may be achieved, when, e.g., a stepper motor is used as valve actuator. Since further movement of the valve driver coupler 125 and the shut-off body 126 is not possible, once the filling position or the draining position is reached, further actuation of the stepper motor will result in a detectable step loss. In this way, the filling position and the draining position may be detected without requiring additional sensors.

From FIGS. 4a to 4c and the before-given description, major advantages of using a step switching mechanism for the valve switching become apparent.

As explained before, the rotational position of the valve driver coupler 125 and—accordingly—of the shut-off body 126 is well defined and locked for all rotational positions of the valve driver 225 where the meshing pin 225c dos not engage any of the meshing slots 125c. This holds true independent of the specific orientation of the valve driver 225 and in particular the meshing pin 225c. This is the case for the area indicated by letter "B" in FIG. 4, corresponding to a rotational angle of about 180°, i.e., half of a full rotation of the valve driver 225. When switching between the filling and the draining position, respectively, it is accordingly irrelevant, at what exact rotational position the valve driver 225 starts its movement and finally stops after the switching, as long as the full sequences of engagements and disengagements between the meshing pin 225c and the meshing slots 125 is ensured. Thereby, the precision requirements for the valve drive and its control are significantly reduced.

A step switching mechanism is further favorable with respect to the coupling of dosing unit 100 and the drive unit 200. As described before, this process is carried out by a user, e.g., a diabetic, without special mechanical skills and in many cases movement disorders and/or visual handicaps, on a routine basis. As long as the meshing pin 225c is in an disengaged state, the only coupling between the valve driver 225 and the valve driver coupler 125 is given by a sliding engagement between the central pin 225b and a peripheral circular face 125b. Therefore, coupling engagement between the dosing unit mounting structure 195 and the drive unit mounting structure 295 can be established by a simple translational movement of the dosing unit 100 relative to the drive unit 200, without requiring a particular orientation or rotational position of the valve driver 225. By coupling the dosing unit 100 to the drive unit 200 in this way, a correct operational position and thereby operative coupling of the valve driver 225 and the valve driver coupler 125 is automatically established.

The before-described advantages of a step switching mechanism is best understood form the comparison with the alternative of coupling via an angle-preserving coupling, e.g., a pair of spur wheels as valve driver and valve driver coupler and valve drive. Such a coupling requires a precise relative orientation of the coupling element. A coupling via toothed wheels, e.g., spur wheels, e.g., requires a tooth of one of the wheels to be aligned with a tooth gap of the other wheel for establishing correct meshing engagement.

The favorable properties of a step switching mechanism for driving the valve movement are closely related to the general property of suited step switching mechanisms that the driving or input element (valve driver) and the driven or output element (valve driver coupler) are in meshing engagement only temporary for the switching and over part of a full rotation of the driving or input element, and disengaged otherwise. For typical angle-preserving gears, such as spur gears, in contrast, the driving or input element and the driven or output element are in continuous meshing engagement. Therefore, other types of step switching mechanisms, as used, e.g., in large variety in clockworks and watches, in movie cameras and projectors, in chemical/medical analyzers or in the pen-changing mechanism of plotters, may be adapted for the purpose of valve switching as well.

The properties of a step switching mechanism are also favorable in comparison with alternative couplings that do not require special alignment, such as frictional coupling via a pair of friction wheels, which are general critical and therefore susceptible to faults due to unintentional friction reduction, e.g., due to production and coupling tolerances, lubricants, and wear.

Coupling the dosing unit 100 and the drive unit 200 in the before-described way, however, requires a rotational position of the valve driver coupler 125 where either of the peripheral circular faces 125b is coaxially aligned with the central pin 225b. For the shown embodiment, this requirement is fulfilled for both the filling position and the draining position, respectively (with one of them being shown in FIG.

4a, as well as the intermediate position shown in FIG. 4c. Favorably, the shut-off body is in either of the filling position or draining position for the assembly, both of which may be well defined by stops as described before. Since the dosing unit is typically a sterile disposable that is used continuously for a number of days and subsequently discarded, coupling has to be carried out only once for each dosing unit. The dosing units may accordingly be provided by the manufacturer in a defined one of the filling position and the draining position, respectively.

Figure 5A:
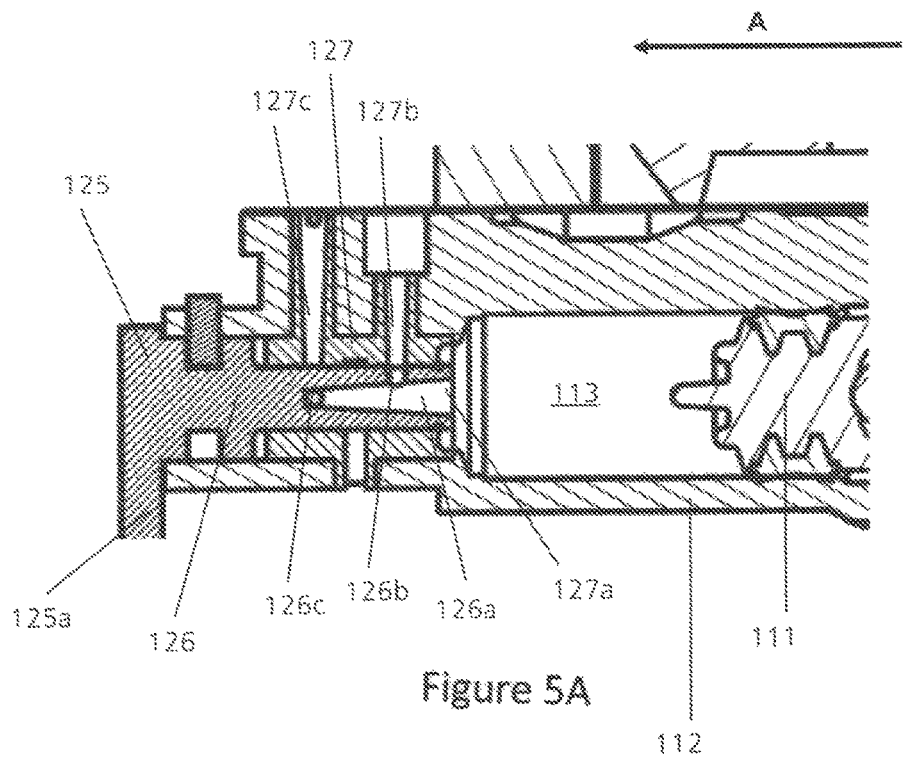
FIGS. 5A, 5B show the internal structure of an exemplary valve unit as well as part of an exemplary pump unit and illustrate their operation.
Figure 5B:
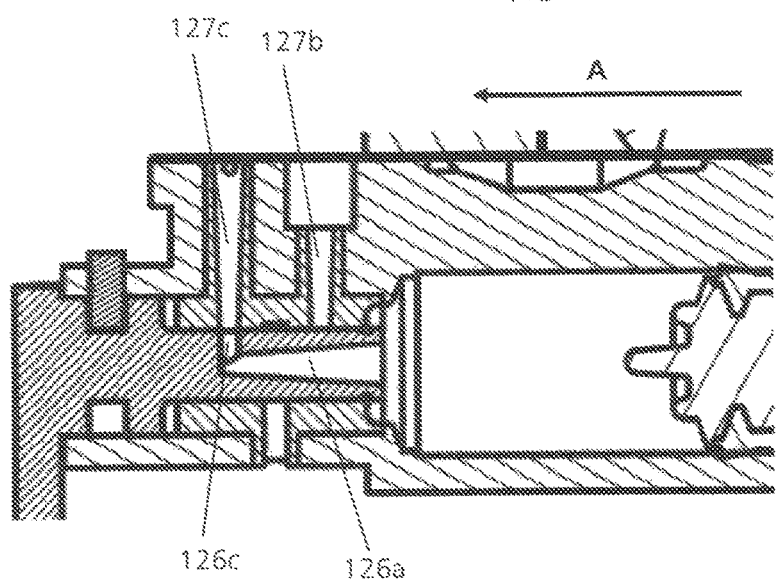

The internal structure of the dosing unit 100, in particular the pump unit 110 and the valve unit 120 as well as its operation is in the following explained with additional reference to FIGS. 5a, 5b, each showing a cross sectional view of a portion of the pump 110 as seen from the top of FIG. 2 with the intersection plane going through the symmetry axis (piston displacement axis and valve rotation axis). FIG. 5a shows the filling state (with the valve body 126 being in the filling position) while FIG. 5b shows the draining state (with the valve body 126 being in the draining position). For the exemplary design of the dosing unit 100, however, it has to be noted the filling state and the draining state are fluidic equivalent and may therefore be interchanged.

As visible from FIG. 5a, 5b, the dosing cylinder 112 exemplarily has a central through bore of changing diameter along its central axis, with the valve housing 127 being sealing arranged in a distal section of the bore and the piston 111 being sealing and sliding arranged in the bore proximal from the valve housing 127. During assembly, the valve unit is accordingly received by the central bore from the distal side and the piston 111 is received by the central bore from the proximal side of the dosing cylinder 112. The proximal front surface of the piston 111 and the distal front surface of the valve housing 127 accordingly define, in combination, a distal and a proximal limiting surface of the metering chamber 113 with the pump port 127a being part of the proximal limiting surface.

As visible from FIG. 5a, the radial channel 126b is, in the filling state, aligned with the filling port 127b which is formed, like the draining port 127c, by a radial fluidic channel or bore in the valve housing 127. In this state, the filling port 127b is accordingly in fluidic coupling with the central channel 126a. The other radial channel 126c is not aligned with a corresponding fluidic channel or bore of the valve housing 127 and is accordingly sealing closed via contact with the valve housing 127.

In the filling state, the dosing cylinder 112 can accordingly be filled with liquid drug by displacing the piston 111 along the piston displacement axis in distal direction opposite to arrow A, thereby increasing and sucking liquid into the metering chamber 113. During this filling process, the valve unit 120 ensures fluidic isolation of the draining port 127c and accordingly of the infusion line 890.

In the draining state that is shown in FIG. 5b, the radial channel 126c is aligned with the draining port 127c. In this state, the draining port 127c is accordingly in fluidic coupling with the central channel 126a. The other radial channel 126b is not aligned with a corresponding fluidic channel of the valve housing 127 and is accordingly sealing closed via contact with the valve housing 127.

In the draining state, the liquid in the metering chamber 113 can accordingly be drained by displacing the piston 111 along the piston displacement axis in proximal direction indicated by arrow A, thereby decreasing and accordingly expelling liquid out of the metering chamber 113. During this draining process, the valve ensures fluidic isolation of the filling port 127b and accordingly of the drug reservoir 300.

Figure 6A:
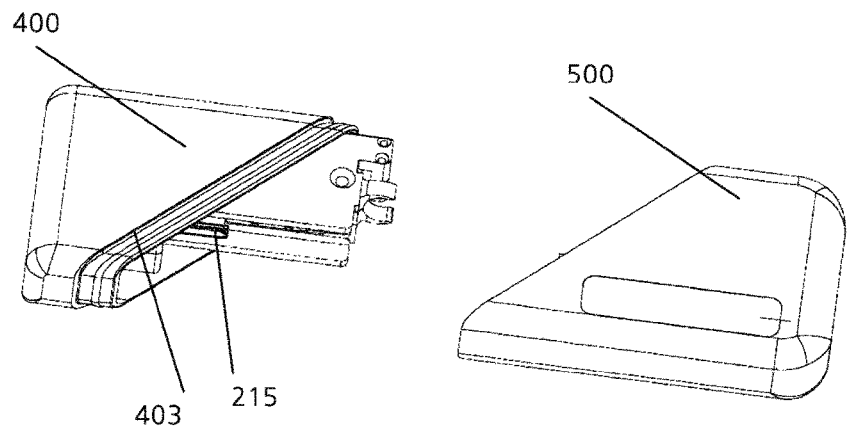
FIGS. 6A, 6B show an exemplary ambulatory infusion system.
Figure 6B:
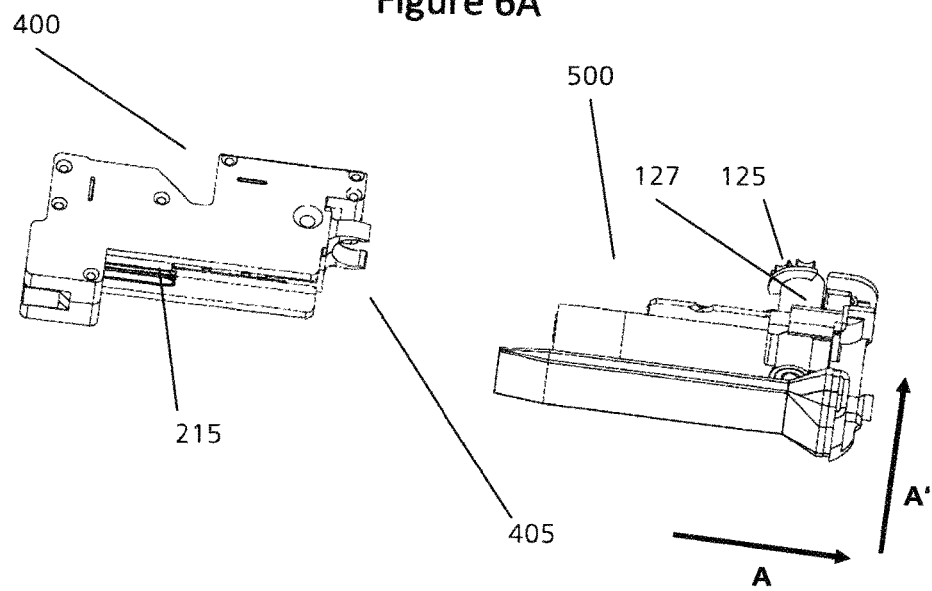

FIG. 6a, 6b, show an exemplary ambulatory infusion system in accordance with the present disclosure. The system includes a durable unit 400 and a disposable unit 500. Both units 400, 500 are shown in a relative orientation that corresponds to the orientation during application, but in an unconnected state as present, e.g., prior to coupling. Coupling of the reusable unit 400 and the disposable unit 500 is achieved by a linear movement of the reusable unit 400 relative to the disposable unit 500 in the direction indicated by arrow A. FIGS. 6a and 6b only differ in that FIG. 6a shows both units 400, 500 with an outer housing or outer shell, while the units 400, 500 are shown without housings in FIG. 6b.

The reusable unit 400 includes a driving unit and may further include components such as user interface, control circuitry, communication interfaces, and the like. A circumferential sealing 403 is provided at the interface to the disposable unit 500 to ensure water tightness or water protection in the assembled states. Sealing may alternatively or additionally be provided at the disposable unit 500. In the following description, elements that are identical or corresponding to elements of the before-described embodiment are assigned the same reference numbers.

The disposable unit 400 includes a dosing unit and a drug reservoir, which may be realized as generally flexible bag or pouch, as, e.g., cylindrical rigid cartridge, or a semi-rigid constructions with rigid and soft or flexible elements. The same types of drug reservoirs may be used in combination with a dosing unit as shown in FIG. 2.

The overall architecture of the dosing ambulatory infusion system and in particular the dosing unit and the drive unit corresponds to the design as shown in FIG. 1. Furthermore, the design generally corresponds to the exemplary design as shown in FIG. 2 to FIG. 5. Some aspects, however, are realized differently, as will be discussed in the following.

In the embodiment of FIG. 6, the drive unit is realized as merely rotational drive, with the pump driver 215 being a reciprocal rotational shaft. The pump driver 225 has, at least on part of its length, a non-circular cross section that may be realized by longitudinal concave elements, e.g., slots, and/or longitudinal protruding elements, such as keys. The pump driver coupler (not shown) of the pump unit has a shape corresponding to the shape of the drive coupler 225 for engagement in rotational direction and substantially friction-free or low-friction sliding engagement in longitudinal direction. Thereby, a driving torque may be transmitted from the pump driver 225 to a pump driver coupler of corresponding cross section with axial sliding engagement and rotational positive locking. The pump driver coupler may be formed by an elongated axial element, arranged distal from sealing piston and pointing away from the metering chamber. The pump driver coupler may be in rigid coupling to or integral with the piston. To transform the rotational movement of the pump driver 225 into a linear, or screw-like movement of the piston, a distal section of the dosing cylinder is provided with a thread, in particular an inner thread, the length of which corresponds at least to the total displacement distance of the plunger. A corresponding outer thread is provided at least one of a section of the pump driver coupler.

In contrast to the embodiment of FIG. 2 to FIG. 5 where the piston displacement axis coincidences with the valve rotation axis, the valve rotation axis, is parallel to arrow A' and perpendicular to the piston displacement axis. Consequently, the valve housing 127 is accordingly also perpendicular to the axis of the dosing cylinder.

For coupling the reusable unit 400 and the disposable unit 500, a snap clamp 405 is provided at the reusable unit. The snap clamp 405 is designed as proximally open ring element and has a diameter to snap-fit around the valve housing 127 which, in this embodiment, simultaneously serves as dosing unit mounting structure. It is to be understood that alternative mounting structures may be used as well, such as a structure corresponding to the one shown in FIG. 2, a magnetic coupling, or the like.

Figure 7A:
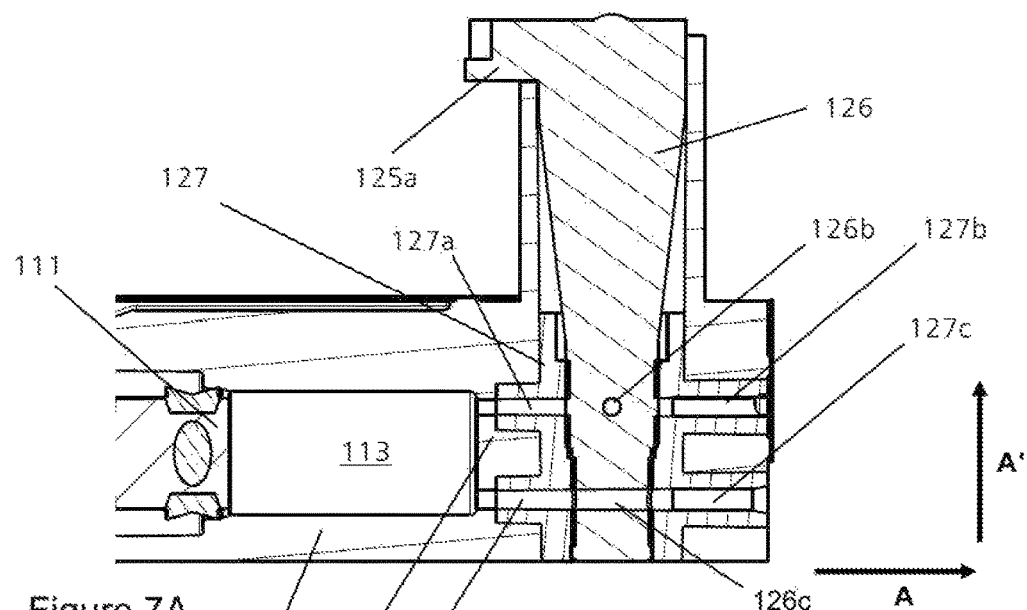
FIGS. 7A, 7B show the internal structure of a further exemplary valve unit as well as part of a further exemplary pump unit and illustrate their operation.
Figure 7B:
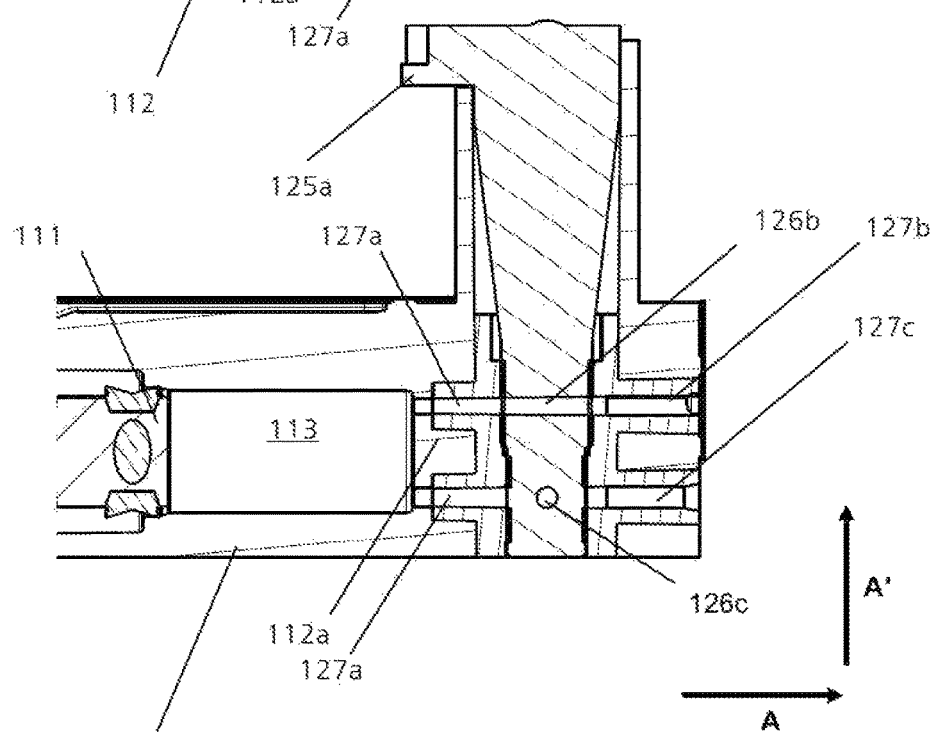

The internal structure of the dosing unit according to this exemplary embodiment 100, in particular the pump unit 110 and the valve unit 120 as well as its operation, is in the following explained with additional reference to FIGS. 7A, 7B, corresponding to FIGS. 5a, 5b for the before-described embodiment. In the embodiment of FIG. 7, the shut-off body 126 only has two radial channels 126b, 126, but no central channel. The radial channels 126b, 126c are designed as through-holes, axially displaced along the symmetry axis of the shut-off body 126 and arranged in an exemplary angle of 90°. Two pump ports 127a are provided, with one of them being aligned with the radial channel 126b in the filling state (FIG. 7A) and the other one being aligned with the radial channel 126c in the draining state (FIG. 7B). Likewise, two corresponding bores (not referenced) are provided in the generally closed proximal front face 112a of the dosing cylinder112, in alignment with the pump ports 127a.

The filling port 127b and the draining port 127c are in this embodiment arranged parallel with the piston displacement axis and perpendicular to the valve rotation axis. For this, design, a straight fluidic connection is given, form the filling port 127b or the draining port 127c, respectively, to the metering chamber 113 via the radial channels 126b or 126c, respectively.

Figure 8:
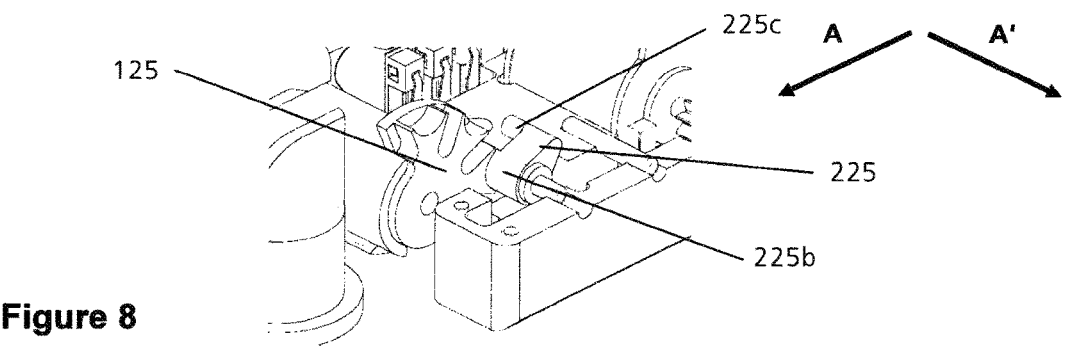
FIG. 8 shows a further exemplary Geneva-type mechanism.

FIG. 8 illustrates the arrangement of the step switching mechanism with valve driver 225 and valve driver coupler 115, exemplarily showing a state without meshing engagement.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

REFERENCE SIGNS

| | |
|---|---|
| 100 | dosing unit |
| 110 | pump unit |
| 111 | piston |
| 112 | dosing cylinder |
| 112a | proximal front face |
| 113 | metering chamber |
| 115 | pump driver coupler |
| 120 | valve unit |
| 120a | valve (draining position) |
| 120b | valve (filling position) |
| 125 | valve driver coupler |
| 125a | Geneva-type segment |
| 125b | peripheral circular face |
| 125c | meshing slot |
| 125d | radial face |
| 126 | shut-off body |
| 126a | central channel |
| 126b, c | radial channels |
| 127a | pump port |
| 127b | filling port |
| 127c | draining port |
| 195 | dosing unit mounting structure |
| 215 | pump driver |
| 217 | pump drive |
| 217a | pump actuator |
| 217b | pump gear |
| 217c | plunger |
| 225 | valve driver |
| 225a | valve driver body |
| 225b | central pin |
| 225c | meshing pin |
| 227 | valve drive |
| 227a | valve actuator |
| 227b | valve gear |
| 295 | drive unit mounting structure |
| 300 | drug reservoir |
| 400 | reusable unit |
| 403 | sealing |
| 405 | snap clamp |
| 500 | disposable unit |
| 890 | infusion line with infusion site interface |
| 900 | patient |

What is claimed is:

1. A dosing unit for an ambulatory infusion system comprising:
    a metering pump unit, the pump unit including a dosing cylinder and a piston, the piston being arranged in sealing sliding engagement inside the dosing cylinder;
    a valve unit, the valve unit having a filling port, the filling port being designed for fluidic coupling with a liquid drug reservoir, a draining port, the draining port being designed for fluidic coupling with an infusion site interface, and a shut-off body, the shut-off body being movable between a filling position where the shut-off body fluidically couples the filling port with the dosing cylinder and an alternative draining position where the shut-off body fluidically couples the dosing cylinder with the draining port; and
    a valve driver coupler, the valve driver coupler being coupled to or integral with the shut-off body and being an output element of a step switching mechanism, wherein, for a first range of motion of a valve driver, the step switching mechanism converts movement of the valve driver to motion of the shut-off body only during a portion of the first range of motion of the valve driver and, during a remaining portion of the first range of motion, movement of the valve driver does not result in motion of the shut-off body.

2. The dosing unit according to claim 1, wherein the valve driver coupler includes a star wheel, a star wheel section, a Geneva-type wheel, or a Geneva-type wheel section.

3. The dosing unit according to claim 1, wherein the shut-off body is designed as a generally cylindrical body.

4. The dosing unit according to claim 1, wherein the shut-off body is made from a hard plastics material, and a shut-off-body contacting surface of a valve housing is made from a soft material, the soft material comprising a rubber or a thermoplastic elastomer.

5. The dosing unit according to claim 1, wherein the shut-off body is designed to move rotationally around a valve rotation axis.

6. The dosing unit according to claim 5, wherein the valve rotation axis is parallel or perpendicular to a piston displacement axis of the pump unit.

7. The dosing unit according to claim 1, wherein the valve driver coupler includes a meshing slot for meshing with a meshing pin of the valve driver which thereby forms a driving element of the step switching mechanism.

8. The dosing unit according to claim 7, wherein the dosing unit is designed for releasable coupling with a drive unit.

9. A drive unit comprising:
a pump drive, the pump drive including a pump actuator and a pump driver coupled to the pump actuator, the pump driver being designed for coupling to a piston of a metering pump unit for transmitting a pump driving force and/or a pump driving torque from the pump actuator to the piston of the pump unit;
a valve drive, the valve drive including a valve actuator and a valve driver coupled to the valve actuator, the valve driver being designed for coupling to a valve driver coupler of a valve unit for transmitting a valve switching force and/or a valve switching torque from the valve actuator to the valve unit; and
wherein the valve driver is a driving element of a step switching mechanism, wherein, for a first range of motion of the valve driver, the step switching mechanism converts movement of the valve driver to motion of a driven element only during a portion of the first range of motion of the valve driver and, during a remaining portion of the first range of motion, movement of the valve driver does not result in motion of the driven element.

10. The drive unit according to 9, wherein the valve driver includes a meshing pin for meshing with the valve driver coupler.

11. The drive unit according to claim 9 wherein the drive unit is designed for releasably coupling with a dosing unit.

12. An ambulatory infusion system for infusing a liquid drug in to a patient's body over an extended time period, the infusion system including the drive unit according to claim 11 wherein the dosing unit comprises:
the metering pump unit, the metering pump unit including a dosing cylinder and the piston, the piston being arranged in sealing sliding engagement inside the dosing cylinder;
the valve unit, the valve unit having a filling port, the filling port being designed for fluidic coupling with a liquid drug reservoir, a draining port, the draining port being designed for fluidic coupling with an infusion site interface, and a shut-off body, the shut-off body being movable between a filling position where the shut-off body fluidically couples the filling port with the dosing cylinder and an alternative draining position where the shut-off body fluidically couples the dosing cylinder with the draining port;
the valve driver coupler, the valve driver coupler being coupled to or integral with the shut-off body and being an output element of the step switching mechanism and wherein the valve driver coupler includes a meshing slot for meshing with a meshing pin of the valve driver which thereby forms the driving element of the step switching mechanism and wherein the shut-off body is the driven element; and
wherein the dosing unit is designed for releasable coupling with the drive unit.

13. The ambulatory infusion system according to claim 12, wherein the valve driver and the valve driver coupler are in a non-meshing state upon coupling the dosing unit and the drive unit.

14. A method for coupling a dosing unit for an ambulatory infusion system and a drive unit for the ambulatory infusion system, the method including:
providing the dosing unit wherein the dosing unit includes:
a metering pump unit, the pump unit including a dosing cylinder and a piston, the piston being arranged in sealing sliding engagement inside the dosing cylinder;
a valve unit, the valve unit having a filling port, the filling port being designed for fluidic coupling with a liquid drug reservoir, a draining port, the draining port being designed for fluidic coupling with an infusion site interface, and a shut-off body, the shut-off body being movable between a filling position where the shut-off body fluidically couples the filling port with the dosing cylinder and an alternative draining position where the shut-off body fluidically couples the dosing cylinder with the draining port; and
a valve driver coupler, the valve driver coupler being coupled to or integral with the shut-off body and being an output element of a step switching mechanism;
providing the drive unit wherein the drive unit includes:
a pump drive, the pump drive including a pump actuator and a pump driver coupled to the pump actuator, the pump driver being designed for coupling to the piston of the metering pump unit for transmitting a pump driving force and/or a pump driving torque from the pump actuator to the piston of the pump unit;
a valve drive, the valve drive including a valve actuator and a valve driver coupled to the valve actuator, the valve driver being designed for coupling to the valve driver coupler of the valve unit for transmitting a valve switching force and/or a valve switching torque from the valve actuator to the valve unit; and
wherein the valve driver is a driving element of the step switching mechanism, wherein, for a first range of motion of the valve driver, the step switching mechanism converts movement of the valve driver to motion of the shut-off body only during a portion of the first range of motion of the valve driver and, during a remaining portion of the first range of motion, movement of the valve driver does not result in motion of the shut-off body;
providing the drive unit and the dosing unit as structurally distinct units; and carrying out a coupling movement, the coupling movement bringing the drive unit and the metering pump unit into an operational relative position, the coupling movement further bringing the valve driver and the valve driver coupler into an operational relative position, wherein the valve driver and the valve driver coupler are in a non-meshing configuration during the coupling movement.

* * * * *